United States Patent [19]

DiMarchi et al.

[11] Patent Number: 4,745,178

[45] Date of Patent: May 17, 1988

[54] PROCESS FOR SELECTIVE PEPTIDE BOND CLEAVAGE USING SULFOXIDES AND $CF_3COOH$

[75] Inventors: Richard D. DiMarchi; Harlan B. Long, both of Carmel, Ind.

[73] Assignee: Eli Lilly and Company, Indianapolis, Ind.

[21] Appl. No.: 41,162

[22] Filed: Apr. 22, 1987

[51] Int. Cl.$^4$ ............................................. C07K 17/00
[52] U.S. Cl. .................................. 530/345; 530/303; 530/308; 530/329; 530/344; 530/397; 530/399; 530/406; 530/408; 530/410
[58] Field of Search ............... 530/303, 308, 344, 345, 530/397, 399, 406, 410, 408, 329

[56] References Cited

U.S. PATENT DOCUMENTS 4,644,057 2/1987 Bicker et al. ...................... 530/409

OTHER PUBLICATIONS

Shechter, Y., Patchornik, A., and Burstein, Y., *Biochem.* 15, 5071–5075 (1976).
Lischwe, M. A., and Sung, M. T., *J. Biol. Chem.* 252, 4976–4980 (1977).
Savige, W. E., and Fontana, A., *Methods Enzymol,* 47, 459–469 (1977).
Ozols, J., and Gerard, C., *J. Biol. Chem.* 252, 5986–5989 (1977).
Savige, W. E., and Fontana, A., *Methods Enzymol.* 47, 442–453 (1977).
Fontana, A., Savige, W. E., and Zambonin, M., in "Methods in Peptide and Protein Sequence Analysis", (Birr, C., Ed.) Elsevier/North-Holland Biomedical Press, 309–322 (1980).
Fontana, A., in "Biochemical and Medical Aspects of Tryptophan Metabolism", (Hayaishi, O., Ishimura, Y., and Kido, R., Editors) Elsevier/North-Holland Biomedical Press, 59–72 (1980).
Huang, H. V., Bond, M. W., Hunkapillar, M. W., and Hood, L. E., *Methods Enzymol.* 91, 318–324 (1983).
Fontana, A., *Methods Enzymol.* 25, 419–423 (1972).

*Primary Examiner*—Howard E. Schain
*Attorney, Agent, or Firm*—William C. Martens; Leroy Whitaker

[57] ABSTRACT

This application describes a process for selectively cleaving a peptide or protein at one or more of its tryptophan residues. The process comprises treating in trifluoroacetic acid said peptide or protein at a concentration of from about 0.05 mM to about 50 mM with an organic sulfoxide at a concentration of from about 0.01M to about 1M, chloride ion at a concentration of from about 0.01M to about 2M, and water at a concentration not in excess of about 10M.

11 Claims, No Drawings

PROCESS FOR SELECTIVE PEPTIDE BOND CLEAVAGE USING SULFOXIDES AND CF₃COOH

BACKGROUND OF THE INVENTION

Selective peptide bond cleavage with chemical reagents has proven to be of immeasurable value in the determination of amino acid sequence. Methionine is the most utilized amino acid site of cleavage due to the exquisite action of cyanogen bromide. The cleavage target of second preference is tryptophan, for which a variety of reagents have been described. Despite more than twenty-five years of investigation, none of the tryptophan reagents can routinely match the cleavage efficiency and selectivity achievable at methionine.

Methods in selective protein cleavage have assumed an increased level of importance with the advent of protein semisynthesis and genetically-engineered protein synthesis. In these areas, utilization of cyanogen bromide has been nearly exclusive. The use of cyanogen bromide for synthetic purposes is precluded when methionine is an inherent residue of a peptide. Several peptides, in particular atrial naturietic factor (ANF), growth hormone releasing factor (GRF), and insulin-like growth factor-I (IGF-I) possess a single methionine and no tryptophan. Each peptide requires a reliable synthetic source for determination of its physiological significance and clinical utility. Currently, the most high-yielding production of peptides in this molecular size is through selective cleavage of an *E. coli*-synthesized fusion protein.

Bacterial synthesis of a fusion protein in which tryptophan immediately precedes a natural peptide devoid of it provides a potential site for selective cleavage. Chemical cleavage at tryptophan peptide bonds is achieved through oxidative halogenation, and has been extensively reviewed. [Fontana, A., Savige, W. E., and Zambonin, M. (1980) In "Methods in Peptide and Protein Sequence Analysis", (Birr, C., Ed.) Elsevier/North-Holland Biomedical Press, 309–322]. Cleavage yields approaching 60% have been attained through the action of BNPS-skatole [2-(2-nitrophenyl-sulfenyl)-3-methyl-3-bromoindolene]. More recently, selective cleavage by a mixture of DMSO and HBr in acetic acid has been recommended [Savige, W. E., and Fontana, A. (1977) *Methods Enzymol.* 47, 459–469]. Modification at tryptophan is not selective by either of these methods. Formation of methionine sulfoxide can occur at near quantitative levels. To a lesser extent, irreversibly modified amino acids such as methionine sulfone, cysteic acid, and/or brominated tyrosine have been observed.

The degree of side-reactions which occur in the course of tryptophan cleavage has been reported to be minimized with the reagent N-chlorosuccinimide (NCS) [Shechter, Y., Patchornik, A., and Burstein, Y. (1976) *Biochem.* 15, 5071–5075]. Methionine conversion to its sulfoxide was the only other modification originally detected. However, in a subsequent study with NCS, appreciable levels of cysteic acid and methionine sulfone were observed [Lischwe, M. A., and Sung, M. T. (1977) *J. Biol. Chem.* 252, 4976–4980]. In amino acid sequence determination, these side-reactions can be distracting but do not preclude successful utilization [Huang, H. V., Bond, M. W., Hunkapillar, M. W., and Hood, L. E. (1983) *Methods Enzymol.* 91, 318–324]. More stringent requirements apply to the use of these reagents during the course of protein synthesis.

Conceptually, tryptophan cleavage with DMSO and HBr in acetic acid is most attractive. Cleavage is selective with reagents that are inexpensive and readily available. More importantly, there is the potential opportunity for immediate regeneration of methionine. Reduction of methionine sulfoxide is achievable in concentrated hydrochloric acid through the addition of dimethyl sulfide [Savige, W. E., and Fontana, A. (1977) *Methods Enzymol.* 47, 453–459]. However, due to the deleterious effects of the strong acidic conditions on peptide structure, these approaches to tryptophan cleavage and methionine sulfoxide reduction are rarely used. In principle, if an appropriate solvent were identified, DMSO-promoted tryptophan cleavage could be rapidly followed by DMS-induced methionine regeneration.

Efficient cleavage at tryptophan cannot be achieved with DMSO and 4N hydrochloric acid in acetic acid [Savige, W. E., and Fontana, A. (1977) *Methods Enzymol.* 47, 442–453]. The action of a more potent halogenating agent such as HBr is required. Unfortunately, its presence also results in an undesirable increase in the level of cysteic acid.

Thus, it is of great importance to develop a process which will afford efficient cleavage at tryptophan while minimizing formation of undesirable by-products and especially by-products that are irreversible.

Such a process has now been discovered. It retains the use, as in prior art processes, of DMSO and HCl. However, instead of carrying out the cleavage in acetic acid, trifluoroacetic acid is employed. Substantial levels of tryptophan cleavage occur but with minimal production of irreversible side products, in particular, minimal conversion of cysteine to cysteic acid and of methionine to methionine sulfone.

SUMMARY OF THE INVENTION

Thus, this invention is directed to a process for selectively cleaving a peptide or protein at one or more tryptophan residues, which comprises treating in trifluoroacetic acid said peptide or protein at a concentration of from about 0.05 mM to about 50 mM with an organic sulfoxide at a concentration of from about 0.01M to about 1M, chloride ion at a concentration of from about 0.01M to about 2M, and water at a concentration not in excess of about 10M.

DETAILED DESCRIPTION OF THE INVENTION

As indicated in the foregoing, this invention is directed to a process for selectively cleaving a peptide or protein at one or more tryptophan residues. The process can be used in any of a number of specific applications, including, for example, structure analysis. Typically, however, the process will find large scale commercial application in the generation of mature protein from a precursor product obtained from recombinant DNA expression. The precursor will be one specifically tailored to have a tryptophan residue located at the amino terminus of the desired mature product linking the mature product to extraneous peptide. The extraneous peptide generally is included for efficiency of expression and/or ease of purification.

In addition, the precursor may be comprised of multiple sequences of mature product, each of which is joined by a tryptophan residue.

In the context of the foregoing, it of course is important that the desired mature product be devoid of tryptophan residues. Examples of biologically active mature products that meet this criterion are insulin-like growth factor-I (IGF-I), insulin-like growth factor-II (IGF-II), growth hormone releasing factor (GRF), atrial natriuretic factor (ANF), proinsulin, insulin A-chain, insulin B-chain, transforming growth factor-α (TGF-α), and the like.

The process of this invention is carried out in trifluoroacetic acid as solvent. Although water is essential for the cleavage and ideally should be present in an amount representing at least one mole per mole of tryptophan residue, a large excess of water is detrimental. Therefore, since in the ordinary course, sufficient water will be added to the reaction mixture upon the addition of a requisite amount of concentrated hydrochloric acid, it is highly preferred to employ substantially anhydrous trifluoroacetic acid. It is not intended by the term "substantially anhydrous" trifluoroacetic acid to require affirmative measures to preclude the presence of trace amounts of water. Only the avoidance of an affirmative addition of water is intended.

To the trifluoroacetic acid are added the protein or peptide to be subjected to cleavage along with an organic sulfoxide and chloride ion. The reagents can be added in any order. Ideally, however, the protein or peptide is first dissolved in the trifluoroacetic acid after which the organic sulfoxide is added followed by chloride ion.

The amount of peptide or protein added to the trifluoroacetic acid generally will range from about 0.05 mM to about 50 mM. Preferably, the concentration will range from about 0.1 mM to about 10 mM. More preferably, from about 0.3 mM to about 3 mM, and most preferably, from about 0.5 mM to about 1.5 mM. The optimal concentration is about 1 mM.

The protein or peptide is reacted in trifluoroacetic acid with an organic sulfoxide and chloride ion. Any of a wide range of organic sulfoxides can be employed, the only requirement being that, apart from the reactive sulfoxide moiety, they be inert under the conditions of the process of this invention. Examples of typical sulfoxides are dimethyl sulfoxide, diethyl sulfoxide, ethyl methyl sulfoxide, diphenyl sulfoxide, methionine sulfoxide, and the like. Preferred sulfoxides are dialkyl sulfoxides in which each alkyl group contains from 1 to 3 carbon atoms. Highly preferred for use in the process of this invention is dimethyl sulfoxide.

The organic sulfoxide is added to the reaction mixture at a concentration ranging generally from about 0.01M to about 1M. The concentration preferably is from about 0.05M to about 0.5M, and, optimally, is about 0.1M.

A remaining essential reagent is chloride ion. The chloride ion can be from any of a wide range of sources. It can, for example, be added as an inorganic salt, an organic salt, hydrogen chloride, and the like. It is highly preferred that the chloride ion be present in a form that is soluble in the medium of reaction, i.e., trifluoroacetic acid. Thus, it is advantageous to employ hydrogen chloride or an organic salt, for example, tetraethylammonium chloride, and the like. Since the cleavage can be conveniently, successfully, and economically carried out using hydrogen chloride, it is the reagent of choice in the process of this invention. When hydrogen chloride is employed, it can be incorporated into the mixture as a gas or it can be added as aqueous hydrochloric acid. In general, the concentration of chloride ion present in the mixture will range from about 0.01M to about 2M, and, preferably, from about 0.05M to about 0.5M. Optimally, the concentration is about 0.1M.

As indicated in the foregoing, water is required for the process of this invention; however, for optimal results, the amount of water must be carefully controlled. For completeness of reaction, water must be present in an amount representing stoichiometry based upon the number of tryptophan residues in the protein or peptide. A lesser amount of water, of course, can be employed with a correspondingly lesser extent of reaction. A substantially excessive amount of water is highly detrimental to the success of the process of this invention. Thus, the water concentration generally should not exceed about 10M.

Advantageously, the desired water concentration can be achieved by the use of concentrated hydrochloric acid which inherently carries a water concentration of approximately four times that of the HCl. Correspondingly, however, if gaseous hydrogen chloride or another chloride ion source is employed, it may be necessary to add water to the reaction mixture to achieve the desired concentration.

The process of this invention can be conducted over a wide temperature range, for example, anywhere from about 5° C. to about 45° C. Preferably, the reaction is conducted at about room temperature (about 20° C. to about 25° C.).

The cleavage normally occurs quite rapidly. Although the reaction can be conducted for an extended period, e.g., about 6 hours, it can be completed in as little as 5 minutes. Customarily, therefore, the reaction is conducted for a period of from about 30 minutes to about 90 minutes.

Upon completion of the cleavage reaction, the desired product can be recovered using recognized recovery techniques. In distinction from prior art processes, the product will include little, if any, oxidation of cysteine to irreversible cysteic acid or methionine to irreversible methionine sulfone. Although some methionine sulfoxide may form under the cleavage conditions of this invention, reduction to methionine is readily available by any of a number of recognized reduction methods.

The following examples are provided to illustrate the process of this invention. They are not intended to be limiting upon the broad scope thereof.

EXAMPLE 1

Treatment of Selected Hexapeptides

The following hexapeptides were prepared:
(1) H-Phe-Trp-Gly-Pro-Glu-Thr-NH$_2$ (FWGPET-NH$_2$)
(2) H-Phe-Cys-Gly-Pro-Glu-Thr-NH$_2$ (FCGPET-NH$_2$)
(3) H-Phe-Met-Gly-Pro-Glu-Thr-NH$_2$ (FMGPET-NH$_2$)

Each was treated in accordance with the process of this invention to evaluate, respectively, the extent of Trp cleavage, Cys oxidation, and Met oxidation.

A specific example of the reaction is as follows:
FWGPET-NH$_2$ (8.32 mg) was solubilized in 7.6 ml anhydrous trifluoroacetic acid (TFA) (1 mg/ml; 1.4 mM). The peptide solution was divided into six portions. One portion received no DMSO or HCl (control). To the other five peptide solutions were added various amounts of DMSO (0.01M to 1M) and concentrated HCl (0.01M to 1M). The solutions were mixed vigorously and then allowed to remain unstirred for 60 minutes at room temperature. The reactions were terminated by rapidly drying with $N_2$ and diluting with 0.1% aqueous TFA. The extent of chemical modification was assessed by high performance liquid chromatography (HPLC) with an (0.46×25 cm) Altex Ultrasphere ODS reversed-phase column. Chromatography was performed in 0.1% TFA at 45° C. with elution achieved through an increasing linear gradient of $CH_3CN$. Quantitation was based on peak area measurements at 214 nm. The DMSO/TFA/HCl-treated FWGPET-$NH_2$ yielded a peptide which displayed an identical chromatographic retention time to that of a synthetic GPET-$NH_2$ standard.

The results using a variety of reagent ratios and each of the foregoing peptides are displayed in Tables 1 and 2 following.

TABLE 1

| Cleavage/Oxidation - DMSO Concentration | | | | | |
|---|---|---|---|---|---|
| Concentration, M (based on TFA) | | | FWGPET—$NH_2$ | FCGPET—$NH_2$ | FMGPET—$NH_2$ |
| DMSO | HCl | $H_2O$ | % Cleaved | % Oxidized[a] | % Sulfoxide[b] |
| — | 0.01 | 0.04 | 0 | 0 | 0 |
| 0.01 | 0.01 | 0.04 | <1 | <0.1 | 24 |
| 0.1 | 0.01 | 0.04 | 67 | <0.1 | 72 |
| 1.0 | 0.01 | 0.04 | 39 | 1.0 | 87 |
| — | 0.1 | 0.4 | 0 | 0 | 7 |
| 0.01 | 0.1 | 0.4 | 83 | <0.1 | 53 |
| 0.1 | 0.1 | 0.4 | 83 | <0.1 | 84 |
| 1.0 | 0.1 | 0.4 | 49 | 0.8 | 96 |
| — | 1.0 | 4.0 | 0 | 0 | 7 |
| 0.01 | 1.0 | 4.0 | 71 | <0.1 | 39 |
| 0.1 | 1.0 | 4.0 | 75 | 1.0 | 71 |
| 1.0 | 1.0 | 4.0 | 41 | 5.5 | 91 |
| 0.1 | — | — | 0 | 0 | 0 |

[a]Oxidation quantitated by reversed phase analysis against the synthetic standard FCGPET—$NH_2$ in cysteic acid form.
[b]Oxidation quantitated by reversed phase analysis against the synthetic standards FMGPET—$NH_2$ and FM(O)G-PET—$NH_2$.

TABLE 2

| Cleavage/Oxidation - HCl/$H_2O$ Concentration | | | | | |
|---|---|---|---|---|---|
| Concentration, M (based on TFA) | | | FWGPET—$NH_2$ | FCGPET—$NH_2$ | FMGPET—$NH_2$ |
| HCl | $H_2O$ | DMSO | % Cleaved | % Oxidized[a] | % Sulfoxide[b] |
| — | — | — | 0 | 0 | 0 |
| 0.01 | 0.04 | — | 0 | 0 | 0 |
| 0.1 | 0.4 | — | 0 | 0 | 7 |
| 1.0 | 4.0 | — | 0 | 0 | 7 |
| — | — | 0.01 | 0 | 0 | 3 |
| 0.01 | 0.04 | 0.01 | <1 | <0.1 | 24 |
| 0.1 | 0.4 | 0.01 | 83 | <0.1 | 53 |
| 1.0 | 4.0 | 0.01 | 71 | <0.1 | 39 |
| — | — | 0.1 | 0 | 0 | 18 |
| 0.01 | 0.04 | 0.1 | 67 | <0.1 | 72 |
| 0.1 | 0.4 | 0.1 | 83 | <0.1 | 84 |
| 1.0 | 4.0 | 0.1 | 76 | 0.8 | 71 |
| — | — | 1.0 | 0 | 0 | 40 |
| 0.01 | 0.04 | 1.0 | 39 | 1.0 | 87 |
| 0.1 | 0.4 | 1.0 | 49 | 0.8 | 96 |
| 1.0 | 4.0 | 1.0 | 41 | 5.5 | 91 |
| 0.1 | 4.0 | 0.1 | 43 | 0.5 | 0 |

[a]Oxidation quantitated by reversed phase analysis against the synthetic standard FCGPET—$NH_2$ in cysteic acid form.
[b]Oxidation quantitated by reversed phase analysis against the synthetic standards FMGPET—$NH_2$ and FM(O)G-PET—$NH_2$.

The following Table 3 displays results obtained with the foregoing three hexapeptides using the process of this invention and several prior art processes.

TABLE 3

| | Cleavage/Oxidation - Selected Methods[a] | | |
|---|---|---|---|
| | FWGPET—$NH_2$ | FCGPET—$NH_2$ | FMGPET—$NH_2$ |
| Method | % Cleaved[c] | % Oxidized[d] | % Sulfoxide[e] |
| NCS/12M HOAc (aq.)[b] | 83 | 16 | 80 |
| BNPS-skatole/12M HOAc (aq.)[b] | 99 | 4 | 100 |
| DMSO-HCl—HOAc/DMSO-HBr[f] | 57 | 72 | 84 |

TABLE 3-continued

| | Cleavage/Oxidation - Selected Methods[a] | | |
|---|---|---|---|
| Method | FWGPET—NH$_2$ % Cleaved[c] | FCGPET—NH$_2$ % Oxidized[d] | FMGPET—NH$_2$ % Sulfoxide[e] |
| DMSO-HCl—TFA[g] | 73 | <1 | 92 |

[a]All reactions conducted for 60 minutes at room temperature, peptide concentration of 1 mg/ml (1.4 mM).
[b]10-fold reagent, relative to peptide.
[c]Cleavage quantitated by reversed-phase analysis against a synthetic GPET—NH$_2$ standard.
[d]Oxidation to cysteic acid quantitated by reversed-phase analysis against synthetic FCGPET—NH$_2$ in cysteic acid form.
[e]Sulfoxide quantitated by reversed-phase analysis against an appropriate synthetic standard, FM(O)GPET—NH$_2$.
[f]Peptide added to mixture of 600 μl HOAc, 25 μl DMSO, and 300 μl HCl (final concentration 12M:0.3M:4M). After 30 minutes added 5 μl HBr and 1.2 μl DMSO (final concentration 1M:0.3M) to 46 μl of the above and maintained 30 minutes.
[g]Peptide added to mixture of 980 μl TFA, 10 μl DMSO, and 10 μl HCl (final concentration 13M TFA, 0.1M DMSO, 0.1M HCl, 0.4M H$_2$O).After 30 minutes, 10 μl DMSO and 10 μl HCl (final concentration 0.1M HCl, 0.1M DMSO, 0.4M H$_2$O) added and mixture maintained 30 minutes.

EXAMPLE 2

Treatment of Insulin B-chain S-sulfonate

Insulin B-chain S-sulfonate (3.84 mg) was dissolved in 3.45 ml of anhydrous trifluoroacetic acid (TFA). To this solution were added 345 μl of DMSO and 34.5 μl of concentrated HCl. The solution was mixed vigorously and then allowed to remain unstirred for 2 hours at room temperature. The reaction was terminated by rapidly drying the mixture with N$_2$. The sample was dissolved in 10% HOAc and purified over a Sephadex G-10 column. The purified peptide was lyophilized and then submitted for amino acid analysis. The cysteic acid level was determined to be 1.6%.

EXAMPLE 3

Oxidation of GRF(1-45),Lys$^{45}$-OH to GRF(1-45),Lys$^{45}$,Met$^{27}$(0)-OH

Growth hormone releasing factor analog [GRF(1-45), Lys$^{45}$-OH] (1.25 mg) was solubilized in 1 ml of anhydrous trifluoroacetic acid (TFA). A 10 μl aliquot of the peptide solution was removed and diluted with 0.1% aqueous TFA to a concentration of 0.05 mg GRF analog/ml. This solution was used as an untreated control. To the peptide/TFA solution were added 100 μl of DMSO, followed by 10 μl of concentrated HCl. The solution was mixed vigorously and then allowed to remain unstirred for 60 minutes at room temperature. The reaction was terminated by a 20-fold dilution with 0.1% aqueous TFA. The extent of chemical modification was assessed by high performance liquid chromatography (HPLC) with a (0.46×15 cm) Vydac C18, reversed-phase column. Chromatography was performed in 0.1% TFA at 45° C. with elution achieved through an increasing linear gradient of CH$_3$CN. Quantitation was based on peak area measurements at 214 nm. The modified GRF analog had a chromatographic retention time identical to that of a synthetic standard GRF analog, Met$^{27}$(O)-OH. The modified material had no measurable unreacted GRF analog present (as compared to the control), and, additionally, the quality of the modified material was comparable to that of the control. Nearly quantitative conversion of GRF analog to its methionine sulfoxide derivative was achieved by this above-described process.

EXAMPLE 4

Oxidation and Cleavage of Glucagon

Glucagon (3.35 mg) was solubilized in 0.27 ml anhydrous trifluoroacetic acid (TFA). The peptide solution was split, one portion being made 1M in DMSO and the other 0.1M (favored). Concentrated HCl was then added to achieve a concentration of 0.1M. The solutions were mixed vigorously and then allowed to remain unstirred for 60 minutes at room temperature. The reactions were terminated by a 20-fold dilution with 0.1% aqueous TFA. The extent of chemical modification was assessed by high performance liquid chromatography (HPLC) with an (0.46×25 cm) Altex Ultrasphere ODS reversed-phase column. Chromatography was performed in 0.1M ammonium phosphate, pH 2.6, at 45° C. with elution achieved through an increasing linear gradient of CH$_3$CN. Quantitation was based on peak area measurements at 214 nm. The yield in cleavage and oxidation of glucagon was quantitated by analysis against synthetic standards of the expected cleavage products, H-Leu-Met(O)-Asn-Thr-OH [LM(O)NT] and H-Leu-Met-Asn-Thr-OH (LMNT). Under the favored conditions 64% cleavage was attained of which the oxidized LM(O)NT accounted for 37% of the total cleaved product.

EXAMPLE 5

Oxidation and Cleavage in Chimeric IGF-1

IGF-1 granules (11.7 mg) [see Williams, D. C., Van Frank, R. M., Muth, W. L., and Burnett, J. P. (1982) Science 215, 687–689] were solubilized in 1.15 ml of anhydrous trifluoroacetic acid (TFA). To this solution were added 11.5 μl of DMSO and 11.5 μl of concentrated HCl. After vigorous initial stirring the sample was allowed to stand unstirred for 60 minutes at room temperature. The reaction was terminated by rapidly drying with N$_2$. The peptide was solubilized in 50% HOAc and purified on a Sephadex G-10 column. After lyophilization the purified sample was converted to its S-sulfonate derivatives. The effect of the oxidative treatment was assessed by high performance liquid chromatography (HPLC) with two (4×0.6 cm) Du-Pont Reliance C$_8$, 3μ, reversed-phase cartridges (in series). Chromatography was performed in 0.1M, pH 7 (NH$_4$)$_2$HPO$_4$ at 45° C. with elution achieved through an increasing linear gradient of CH$_3$CN. The modified IGF-1 had retention times identical to biosynthetic IGF-1 and IGF-1, Met$^{59}$(O) reference standards. A yield of 2.9% IGF-1 from the impure granules was obtained. The oxidized Met(O)IGF-1 accounted for 54% of the cleaved product.

We claim:
1. A process for selectively cleaving a peptide or protein at one or more tryptophan residues, which comprises treating in trifluoroacetic acid said peptide or protein at a concentration of from about 0.05 mM to about 50 mM with an organic sulfoxide at a concentra- tion of from about 0.01M to about 1M, chloride ion at a concentration of from about 0.01M to about 2M, and water at a concentration not in excess of about 10M.

2. Process of claim 1, which comprises carrying out the cleavage in substantially anhydrous trifluoroacetic acid.

3. Process of claim 2, which comprises carrying out the cleavage using hydrogen chloride as chloride ion source.

4. Process of claim 3, which comprises carrying out the cleavage using concentrated hydrochloric acid as the entire source of both hydrogen chloride and water.

5. Process of claim 4, in which the peptide or protein concentration is from about 0.3 mM to about 3 mM.

6. Process of claim 5, in which the peptide or protein concentration is from about 0.5 mM to about 1.5 mM.

7. Process of claim 3, in which the organic sulfoxide is a dialkyl sulfoxide in which each alkyl group contains from 1 to 3 carbon atoms.

8. Process of claim 7, in which the organic sulfoxide is dimethyl sulfoxide.

9. Process of claim 8, in which the dimethyl sulfoxide concentration is from about 0.05M to about 0.5M.

10. Process of claim 3, in which the hydrogen chloride concentration is from about 0.05M to about 0.5M.

11. Process of claim 2, in which the water content of the reaction mixture is at least that necessary to achieve a stoichiometric equivalent based upon the number of tryptophan residues in the peptide or protein.

* * * * *